United States Patent
Cutting

(10) Patent No.: US 10,005,575 B2
(45) Date of Patent: Jun. 26, 2018

(54) FACILITY AND METHOD FOR PRODUCING A CONTAINER LOADED WITH A BIOPHARMACEUTICAL FLUID

(71) Applicants: SARTORIUS STEDIM NORTH AMERICA INC., Bohemia, NY (US); Jonathan Cutting, Hannover (DE)

(72) Inventor: Jonathan Cutting, Hannover (DE)

(73) Assignee: SARTORIUS STEDIM NORTH AMERICA INC., Bohemia, NY (US)

( * ) Notice: Subject to any disclaimer, the term of this patent is extended or adjusted under 35 U.S.C. 154(b) by 400 days.

(21) Appl. No.: 14/779,141

(22) PCT Filed: Mar. 20, 2014

(86) PCT No.: PCT/EP2014/055564
§ 371 (c)(1),
(2) Date: Sep. 22, 2015

(87) PCT Pub. No.: WO2014/147159
PCT Pub. Date: Sep. 25, 2014

(65) Prior Publication Data
US 2016/0068293 A1     Mar. 10, 2016

(30) Foreign Application Priority Data
Mar. 22, 2013  (FR) ..................... 13 52607

(51) Int. Cl.
*B65B 31/04*     (2006.01)
*B65B 3/00*      (2006.01)
(Continued)

(52) U.S. Cl.
CPC ............ *B65B 31/04* (2013.01); *A01N 1/0252* (2013.01); *A01N 1/0263* (2013.01); *A61J 1/10* (2013.01);
(Continued)

(58) Field of Classification Search
CPC ......... B65B 3/003; B65B 31/00; B65B 31/04; B65B 31/047; B65B 57/10; B65B 63/08;
(Continued)

(56) References Cited

U.S. PATENT DOCUMENTS

| 3,730,500 A | 5/1973 | Richards |
| 3,838,794 A | 10/1974 | Cogley et al. |

(Continued)

FOREIGN PATENT DOCUMENTS

DE    202012005987 U1 * 7/2012 ............ G01M 3/329
EP    1 475 112 A1   11/2004
(Continued)

OTHER PUBLICATIONS

Chinese Office Action issued in Application No. 201480025322.X, dated Apr. 12, 2017.
(Continued)

*Primary Examiner* — Stephen F Gerrity
(74) *Attorney, Agent, or Firm* — Young & Thompson

(57) ABSTRACT

A facility (1) for producing a container loaded with a biopharmaceutical fluid, includes: a container (2) wherein a biopharmaceutical fluid is placed (B); a control module (9) for controlling the filling of gas into the container (2); and an analysis module (10) for estimating a parameter for controlling the gas filling; and a pumping device (40) for generating a depression in the inner filling space (Vg).

19 Claims, 4 Drawing Sheets

(51) Int. Cl.
  *B65B 57/10* (2006.01)
  *B65B 63/08* (2006.01)
  *B65D 81/20* (2006.01)
  *A61J 1/10* (2006.01)
  *A01N 1/02* (2006.01)
  *B65B 31/00* (2006.01)
  *A61J 1/14* (2006.01)
  *A61J 1/16* (2006.01)
  *F25D 3/10* (2006.01)

(52) U.S. Cl.
  CPC .............. *B65B 3/003* (2013.01); *B65B 31/00* (2013.01); *B65B 31/047* (2013.01); *B65B 57/10* (2013.01); *B65B 63/08* (2013.01); *A61J 1/1475* (2013.01); *A61J 1/16* (2013.01); *B65D 81/2061* (2013.01); *B65D 81/2084* (2013.01); *F25D 3/105* (2013.01)

(58) Field of Classification Search
  CPC ........... B65D 81/2023; B65D 81/2038; B65D 81/2061; B65D 81/2084; A01N 1/0252; A01N 1/0263; A61J 1/10; A61J 1/1475; A61J 1/16
  USPC ................. 53/432, 434, 440, 510, 512, 127; 73/31.04
  See application file for complete search history.

(56) References Cited

U.S. PATENT DOCUMENTS

| | | | |
|---|---|---|---|
| 4,243,349 A * | 1/1981 | Hickey et al. | B65D 81/2038 200/83 C |
| 5,099,679 A * | 3/1992 | Huerlimann et al. | G01N 1/2226 73/31.04 |
| 5,163,909 A | 11/1992 | Stewart | |
| 5,399,166 A | 3/1995 | Laing | |
| 5,481,852 A * | 1/1996 | Mitchell | B65B 31/04 53/432 |
| 5,492,534 A | 2/1996 | Athayde et al. | |
| 5,505,708 A | 4/1996 | Atkinson | |
| 5,743,878 A | 4/1998 | Ross et al. | |
| 5,776,104 A | 7/1998 | Guignard et al. | |
| 5,794,408 A * | 8/1998 | Patouraux | B65B 31/04 53/432 |
| 5,799,830 A | 9/1998 | Carroll et al. | |
| 5,988,422 A | 11/1999 | Vallot | |
| 6,112,506 A * | 9/2000 | Eberhardt, Jr. et al. | B65B 31/02 53/510 |
| 6,499,838 B2 | 12/2002 | Seccombe et al. | |
| 7,591,121 B2 * | 9/2009 | Lin | F28D 15/0283 53/127 |
| 2003/0079482 A1 * | 5/2003 | Voute et al. | A01N 1/0263 62/66 |
| 2003/0080126 A1 * | 5/2003 | Voute et al. | A01N 1/0263 220/9.4 |
| 2004/0139700 A1 * | 7/2004 | Powell et al. | B65B 3/003 53/432 |
| 2004/0232171 A1 | 11/2004 | Bobst | |
| 2006/0016155 A1 | 1/2006 | Oesterlein | |
| 2007/0175538 A1 * | 8/2007 | Rothbauer et al. | B65B 31/04 141/59 |
| 2008/0121019 A1 * | 5/2008 | Schlafer | C12M 41/34 73/31.04 |
| 2009/0075362 A1 | 3/2009 | Baumfalk et al. | |
| 2010/0305884 A1 * | 12/2010 | Yudovsky et al. | C23C 16/4481 73/31.04 |
| 2011/0120667 A1 | 5/2011 | Cutting et al. | |
| 2012/0059603 A1 * | 3/2012 | Stering | B01D 46/0086 702/47 |

FOREIGN PATENT DOCUMENTS

| | | |
|---|---|---|
| EP | 1 593 601 A1 | 11/2005 |
| EP | 1 441 585 B1 | 5/2006 |
| EP | 1 441 586 B1 | 6/2006 |
| EP | 2 113 171 A2 | 11/2009 |
| EP | 1 407 202 B1 | 1/2010 |
| EP | 2 101 129 A3 | 8/2015 |
| FR | 2 682 602 A1 | 4/1993 |
| GB | 7 800 29 A | 7/1957 |
| JP | H01159576 A | 6/1989 |
| JP | 2000/044939 A | 2/2000 |
| WO | 94/27659 A1 | 12/1994 |
| WO | 00/04131 A1 | 1/2000 |
| WO | 02/095306 A1 | 11/2002 |
| WO | 02/099487 A1 | 12/2002 |
| WO | 2007/103917 A2 | 9/2007 |
| WO | 2011/001178 A1 | 1/2011 |
| WO | 2011/063381 A2 | 5/2011 |
| WO | 2012/037535 A2 | 3/2012 |
| WO | 2012/044403 A1 | 4/2012 |
| WO | 2012/109029 A1 | 8/2012 |

OTHER PUBLICATIONS

European Search Report issued in Application No. 14 711 255.1, dated Feb. 22, 2017.
International Search Report, dated May 21, 2014, from corresponding PCT application.
FR Search Report. dated Oct. 28, 2013, from corresponding FR application.

* cited by examiner

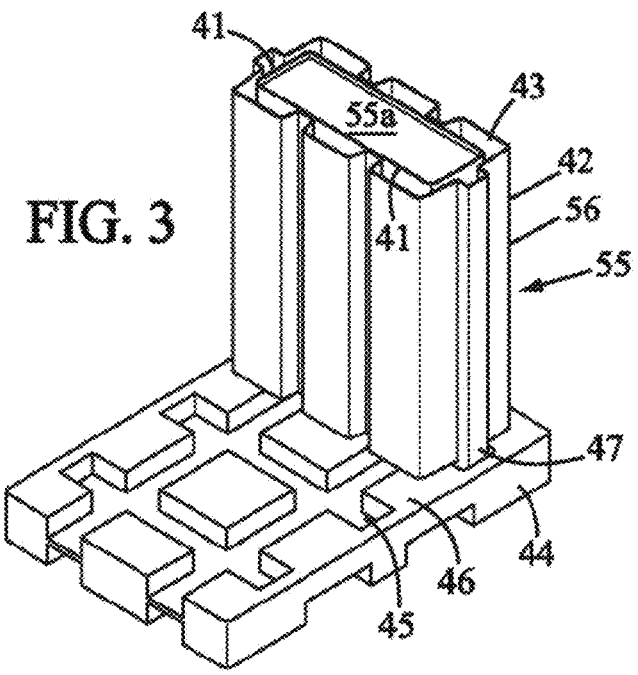
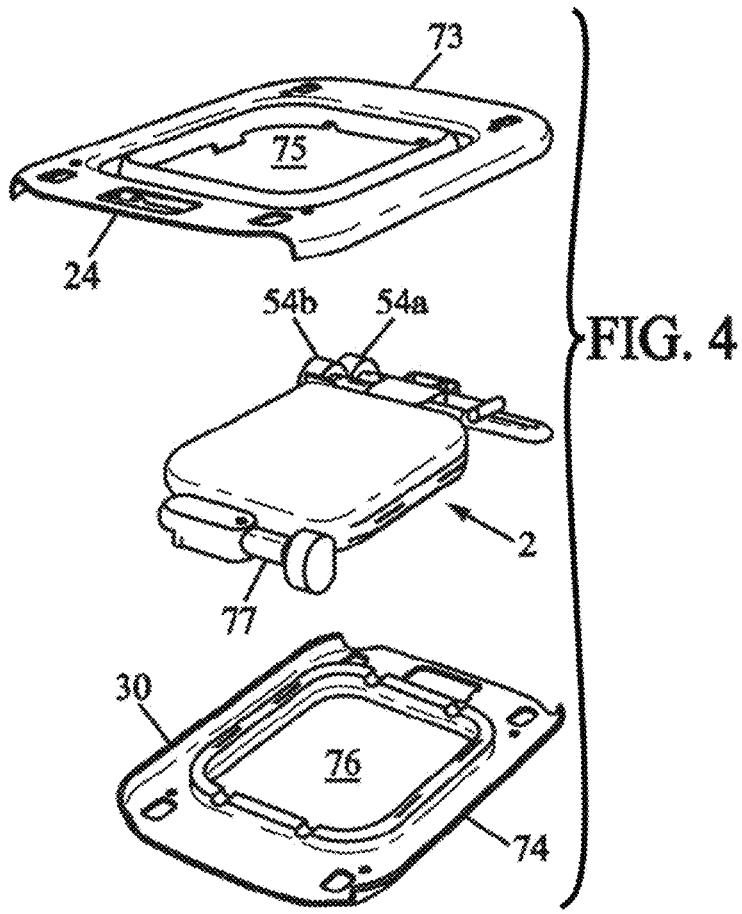

FACILITY AND METHOD FOR PRODUCING A CONTAINER LOADED WITH A BIOPHARMACEUTICAL FLUID

The invention relates to the field of preparing the interior of a sealed container loaded with a biopharmaceutical fluid (partially filled) and a gas, typically air or nitrogen ($N_2$), the container being specially equipped for controlling its filling with said gas. The invention particularly relates to a facility and method for preparing such a type of container partially loaded with a biopharmaceutical fluid, particularly in a frozen state.

In the context of the invention, the term "biopharmaceutical fluid" is understood to mean a fluid derived from biotechnology—culture media, cell cultures, buffer solutions, artificial nutrition liquids, blood fractions and derivatives of blood products—or a pharmaceutical fluid or more generally a fluid for use in the medical field.

A container having a flexible peripheral wall, specially adapted to receive such a biopharmaceutical fluid, is already known and is quite satisfactory. Generally, such a container may be associated with a rigid support structure to form a biopharmaceutical fluid containing means. Such a containing means is described for example in EP 1,441,585. Further examples of such containing means can be found in WO 2007/103917.

To better preserve a biopharmaceutical fluid before a process step or for later use, it has also been proposed to keep it in frozen form. Thermal treatment systems (heat and/or cold) have been provided for this purpose, in particular for freezing the biopharmaceutical fluid contained in the containers. The specific properties of biopharmaceutical fluids have led to the development of containers specially adapted for freezing, for example having a slightly flared shape as described in EP 1,441,586. In a known manner, the biopharmaceutical fluid in a liquid state only partially fills the container, and the latter is pressurized. Moreover, the volume expansion of the biopharmaceutical fluid during freezing can generate excess pressure. Gas is injected into the container prior to freezing so that the excess volume is filled. This gas-filled volume generally corresponds to the headspace when the container is in the form of a bag defining a single common chamber to be filled with the biopharmaceutical fluid and the gas. The fact that the pressure is maintained above a certain threshold ensures that there is physical contact between the top of the container and the inner wall of the thermal treatment system used to obtain a substantially homogeneous freezing of the biopharmaceutical product (refer to WO 2011/063381 for an example of such a thermal treatment system). Freezing may be considered optional, however, as some biopharmaceutical fluids can be stored satisfactorily for a reasonable period without such treatment. It may be noted that even without the effects of expansion/contraction due to freezing/thawing, variations in ambient pressure can also create excess pressure in the container.

It is understood that for a biopharmaceutical fluid storage application, it is preferable for the container to be discarded after use (disposable container). The walls of the container, based on a flexible and gas-impermeable plastic, are therefore as thin as a film in order to reduce the amount of plastic.

To maintain relatively stable container dimensions, it is possible to ensure that the internal gas filling volume (complementary to the volume occupied by the biopharmaceutical fluid) is pressurized in a controlled manner, the level of pressure remaining for example below a threshold of about 100 mbar (1.45 psi), preferably not beyond 50 mbar (0.73 psi).

During transport, the gas occupies an inner filling space within the container which can change due to changes in ambient pressure. If the internal volume for receiving gas is overfilled before freezing or before a decrease in the ambient pressure, then the container could swell to its maximum expansion. Once the maximum expansion is reached, the gas pressure inside the container increases in response to a decrease in the ambient pressure. During this swelling phenomenon (and similarly in case of contraction), the thin walls must move and bend. Such stresses may impact the integrity of the container, with a risk of cracks developing in the plastic in extreme conditions (and the material then remains fragile). This is why movement of the container walls is undesirable and should be avoided.

A description of the invention as characterized in the claims is presented below.

According to a first aspect, the invention relates to a facility for the preparation of a container loaded with a biopharmaceutical fluid, the facility comprising:
- a fluidtight container in which is placed a biopharmaceutical fluid and a gas which occupies an inner filling space, the container comprising a gas passage opening and being adapted to be filled with gas to an initial level of positive pressure in the inner filling space;
- a control module for controlling the filling of the container with gas;
- an analysis module for estimating a gas filling control parameter.

The facility comprises a pumping means for generating a negative pressure in the inner filling space by forcing the gas to flow out of the container via the gas passage opening, the control module and the pumping means being coordinated to adjust the duration of the forced flow on the basis of the control parameter determined by the analysis module.

Thus, the above facility allows knowing the amount of gas that should be discharged in anticipation of variable transport conditions, and also allows selectively removing an amount of gas. For example, to anticipate extreme transport conditions, about 40% of the gas present in the estimated volume may be removed, generating a negative pressure (when freezing, this removal is obviously performed after freezing the pharmaceutical fluid). This threshold of about 40% takes into account the maximum variation in altitude when traveling by land. This variation cannot exceed 3000 meters (on currently existing roads), representing a variation in the external pressure of about 32%. Note also that in the case of air transport, the maximum altitude is typically between 2000 and 4000 meters. For example, the main air shipment companies specify altitudes of less than 3000 meters for a cargo plane: 2438 m (8000 ft). Generating a negative pressure with this threshold of about 40% is perfectly appropriate for air shipment because the amount of gas in the container is insufficient in this case to create a significant positive pressure under the usual altitude conditions.

According to one feature, the control module is adapted to selectively control a flow of released gas through the gas passage opening of the container, so as to reduce the pressure level in the inner filling space.

As the gas filling control parameter is representative of the inner filling space, the analysis module is configured to estimate this control parameter for example by monitoring the flow of released gas, between a first level of positive pressure and a second level of positive pressure in the inner filling space.

The expression "representative of the inner filling space" is understood to mean a parameter equal to the volume occupied by the gas or directly correlated to this volume (for example it may be a height measured vertically between the upper end of the container and the upper level of the biopharmaceutical fluid when the filling volume is a headspace within a container of substantially constant cross-section along a vertical longitudinal axis).

The facility allows reducing the level of positive pressure. One can see that this type of facility is thus suitable for small containers (a few centiliters or less) as well as for large containers (one hundred or several hundred liters at least).

According to other features, the control module is adapted to selectively control a flow of released gas through the gas passage opening of the container, in a manner that reduces the positive pressure in the inner filling space, and the gas filling control parameter is representative of said inner filling space, the analysis module being configured for estimating said control parameter by monitoring the flow of released gas between a first level of positive pressure OP1 and a second level of positive pressure OP2 in the inner filling space.

According to other features, the analysis module comprises or is connected to a timer adapted to determine the duration of the gas release $\Delta t$ required to drop from the first level of positive pressure OP1 to the second level of positive pressure OP2.

According to other features, the analysis module determines, as a control parameter, the inner filling space (Vg) using the following correlation:

$$Vg=Q/k+Vc$$

where:
Vg is the internal volume occupied by the gas;
Q is a volumetric flow rate constant;
Vc is a volume constant;
k is a decay constant;
knowing that the decay constant is calculated using the equation:

$$k=-\ln(OP2/OP1)/\Delta t$$

with
OP1 being the first level of positive pressure inside the container;
OP2 being the second level of positive pressure inside the container;
$\Delta t$ being the duration of the gas release required to drop from the first level of positive pressure OP1 to the second level of positive pressure OP2;
In representing the natural logarithm function.

According to other features, the facility further comprises a plurality of valves comprising valves selectively controlled by the control module and having:
a first configuration permitting the flow of gas in an incoming direction into the container; and
a second configuration permitting the flow of gas in an outgoing direction from the container;
the control module being adapted to successively configure the first configuration to enable the container to be filled with gas to a state of positive pressure within said inner filling space, and the second configuration to enable gas to escape from the container via the gas passage opening at most until a state of pressure equilibrium is reached in said inner filling space.

According to other features, said plurality of valves comprises a first gas inlet valve selectively opened by the control module in the first configuration and a second gas release valve selectively opened by the control module in the second configuration, the gas inlet valve and the gas release valve being in fluid communication with said gas passage opening.

According to other features, the pumping means comprises a vacuum pump and a third gas removal valve that is one among said plurality of valves, the control module being configured for selectively opening the gas removal valve and closing the gas inlet valve and the gas release valve when the vacuum pump is actuated.

According to other features, the analysis module comprises or is connected to a pressure sensor in fluid communication with the gas passage opening and adapted for measuring a level of positive pressure inside the container.

According to other features, the facility according to any one of the preceding claims comprises a gas injection device adapted to inject gas, preferably pressurized, into the container by said gas passage opening prior to the control parameter determination.

According to other features, the gas injection device, the pumping means, and a control unit comprising the control module and the analysis module are incorporated into a device for preparing the interior of the container.

According to other features, the container is flexible and sealed closed, the container comprising gas-impermeable plastic walls.

In another aspect, the invention relates to a method for preparing a sealed container loaded with a biopharmaceutical fluid, a gas occupying an inner filling space inside the container at an initial level of positive pressure, wherein a gas filling level within the container is controlled, the method comprising the steps consisting essentially of:
b) estimating a gas filling control parameter which is representative of said inner filling space,
c) generating a negative pressure in the inner filling space by forcing gas to flow out of the container, the duration of the forced flow being adjusted according to said control parameter.

According to other features, the forced flow is achieved by pumping at a constant flow rate, the forced flow being stopped after a first time limit corresponding to the time required to discharge an amount of gas equal to 30% of the initial amount of gas contained in the inner filling space determined in step b) and before a second time limit corresponding to the time required to evacuate an amount of gas equal to 50% of the initial amount of gas contained in the inner filling space determined in step b).

According to other features, the method further comprises the following step before step b):
a) selectively controlling a flow of released gas through a gas passage opening of the container, so as to lower the positive pressure inside the container; and wherein the estimating in b) includes monitoring the flow of released gas between a first level of positive pressure OP1 and a second level of positive pressure OP2 in the inner filling space.

According to other features, said control parameter is estimated by determining the duration of the gas release $\Delta t$ required to drop from the first level of positive pressure OP1 to the second level of positive pressure OP2.

According to other features, the method comprises, prior to step a), the steps consisting essentially of:
injecting a gas, preferably air or nitrogen, into the container until a positive pressure is reached in the inner filling space of between 10 and 50 mbar; and
freezing the biopharmaceutical fluid.

According to other features, step b) is performed when a gas release valve in fluid communication with the gas passage opening is selectively opened, said gas release valve remaining open until the pressure between the inner filling space and the environment is equalized, several measurements of a parameter of the gas representative of a level of positive pressure in the inner filling space being performed during step b).

The drawings in the figures will now be briefly described.

FIG. 3 is a partial schematic perspective view of a portion of a thermal treatment system.

FIG. 4 is an exploded perspective view of an alternative embodiment of a biopharmaceutical fluid container.

Below is a detailed description of several embodiments of the invention, with examples and with reference to the drawings.

Figure 1:
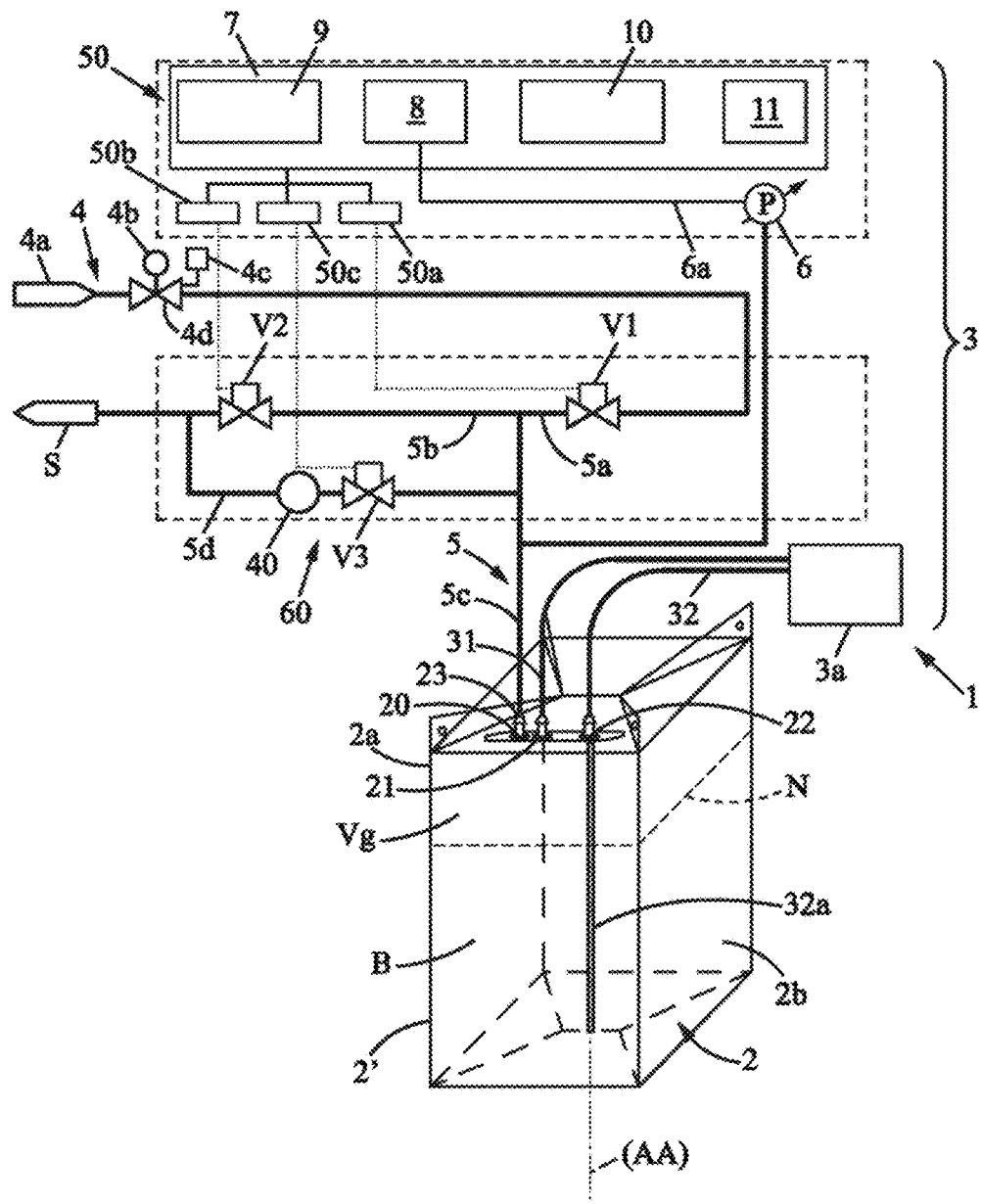
FIG. 1 is a schematic perspective view of a portion of a facility for preparing a container according to a first embodiment.

As can be seen in FIG. 1, the facility 1 comprises a container 2 loaded with a biopharmaceutical fluid B, here in the frozen state, and a device 3 for preparing the interior of the container 2.

The flexible container 2 comprises a flexible envelope 2 which defines an interior space capable of receiving content and here having actually received it.

Such a container 2 is typically a 3D bag comprising two main walls interconnected by and welded to two side gussets, which can be folded flat (particularly for storage and transportation) or unfolded and deployed (for filling with content), the volume of the interior space being at least 1 liter, up to 3000 liters or more. It is understood that this bag embodiment is provided as a purely illustrative example, and that the flexible container can be implemented differently. The principles of the arrangement and construction of such a flexible container 2 are part of the general knowledge of or are within the reach of the skilled person. In all cases, the container 2 has a certain flexibility, being made of a plastic film having a certain flexibility, of a single layer or most often of multiple layers. The film is, however, substantially non-extensible under normal usage conditions, such that the volume of the interior space can be considered constant. This is to ensure the external stability of such a flexible container 2 of large volume, once filled with content, when placed and externally supported within a rigid receiving and support structure.

The flexible container 2, once filled and in position, has a horizontally arranged lower portion 2b, and an upper portion 2a that is also arranged horizontally. It also presents a substantially vertical main axis AA, relative to which the terms "lower," "upper," "side," "horizontal," and "vertical" are applied to the flexible container as a whole. Due to gravity, the fluid, liquid, pasty, or partially solid content will be located primarily in the lower portion 2b of the flexible container 2 during the thermal treatment, while the upper portion 2a will primarily contain a gas at pressure P.

The flexible container 2 is usually provided with ports, for example such as an entry port 21 for admitting or introducing a product to be mixed with the content of the container 2, located in the upper portion 2a of the flexible container 2, an exit port 22 for discharging the mixed product from the container 2, and a gas feed port 20.

The device 3 for preparing the interior of the container may comprise a conventional type of feed device 3a for injecting biopharmaceutical fluid B into the container 2. The feed device 3a is connected to the container 2 by a filling line 31 in fluidtight fluid communication with the entry port 21 of the container 2, for delivering biopharmaceutical fluid into the container 2. The feed device 3a may also have a draining line 32 in fluidtight fluid communication with the exit port 22 of the container 2, for delivering biopharmaceutical fluid from the container 2. In this FIG. 1, the tubing 32a internal to the container 2 and connecting the exit port 22 to the bottom of the container 2 is represented.

The container 2 is of the flexible type; usually the ports 21, 22 of the container 2 each form a connector. In addition to the gas passage opening 20, at least one additional port (not shown in FIG. 1) may be provided for mounting a functional device or measurement means, for example for measuring a parameter indicative of or related to the homogeneity, heterogeneity, or the blending of the content of the interior space.

The device 3 for preparing the interior of the container may optionally include a thermal treatment unit (not shown in FIG. 1) as described in WO 2011/063381, to allow freezing the biopharmaceutical fluid B contained in the container 2. A cavity of the thermal treatment unit has a shape suitable for receiving the container 2.

The biopharmaceutical product B is liquid or pasty overall, at least when it is to be mixed, so as to allow it to be mixed. It may only have one fluid phase or several, including products that are originally solid or have a certain solidity, for mixing with a fluid medium. Such a container 2 is typically intended for the preparation of a biopharmaceutical product, for storage, for transport, or for carrying out a certain process of physical, chemical, or biological nature such as mixing, or bioreactor or system for freezing/thawing.

Either the content is always liquid or pasty, or it is at some point or during a particular period. For example, the content can be in a solid state as a result of a freezing process, or in a fluid state after thawing. In one exemplary embodiment, the facility 1 has means for monitoring the state of the biopharmaceutical fluid B, so as to detect the freezing state and typically a completely frozen state.

When freezing is required, the device 3 for preparing the interior of the container may optionally comprise a monitoring device (not shown) for monitoring the freezing state of the biopharmaceutical fluid B contained in the container 2, for example with temperature sensors and/or with a unit for monitoring the evolution of the freezing front by ultrasound imaging (as described in WO 2012/044403). Such a monitoring device may comprise multiple units placed together in one station or distributed, and also comprises a user interface, for example to display the results of measuring physical parameters inside the container 2.

In this first preparation example, the container 2 is only partially filled with biopharmaceutical fluid B, and the level of fluid in the container 2 is schematically represented by a horizontal dotted line N in FIG. 1. The upper head portion of the container 2 (above the dotted line) is filled with gas by means of a gas injection device 4. The container 2 has at least one gas passage opening 20 or port in fluidtight fluid communication with a connector 23 to which the gas injection device 4 is connected. The connector 23 here is connected to a gas entry/exit line 5 of the gas injection device 4. This gas entry/exit line 5 comprises a gas infeed section 5*a*, a gas outfeed section 5*b* parallel to the gas infeed section 5*a*, and a common section 5*c* which is connected at one end to the gas infeed 5*a* and outfeed 5*b* sections, and is connected at the other end to the gas passage opening 20 via the connector 23. In a known manner, the gas injection device 4 comprises a gas source 4*a*, for example a source of air or nitrogen ($N_2$), which has a fluidtight fluid connection with the gas infeed section 5*a*.

The pressure P of the gas contained in the container 23 may optionally be regulated by a pressure regulation system. One can, for example, use a system such as those used for verifying filter quality. Regulating the pressure inside the container 2 prevents the gas pressure from exceeding a predetermined limit (for example 100 mbar) that could affect the physical integrity of the container 2. In addition, the fact that the pressure is maintained above a certain limit ensures that there is physical contact between the upper portion of the container 2 and the inner wall of the thermal treatment unit. The pressure regulation system comprises, for example, a pressure sensor 6, positioned here at a location in fluid communication with the interior of the container 2.

The device 3 for preparing the interior of the container comprises a control unit 7 adapted to adjust the amount of gas after the previously performed injection by the gas injection device 4 to a pressure level. This control unit 7 may be part of the gas flow control equipment 50. The pressure regulation system may be incorporated into the equipment 50 and the control unit 7 can be coordinated with the pressure regulation system. A memory 8 accessible by the control unit 7 stores pressure data and possibly temperature data. The control unit 7 processes these pressure data and retrieves information representative of the inner filling space Vg occupied by the gas, in order to adjust the amount of gas remaining in the container 2. The control unit 7 may also process such data for display on a screen of a user interface.

A gas inlet valve V1, which is selectively opened by a control module 9 of the control unit 7, is arranged on the gas infeed section 5*a* of the line 5. The gas infeed section 5*a* may also optionally have a pressure sensor 4*b* and a controller 4*c* which are adapted to regulate the pressure of the gas released from the gas source 4*a* to the common section 5*c* of the gas entry/exit line 5. An intake valve 4*d* is also provided, on the gas infeed section 5*a* of the line 5 between the source 4*a* and the inlet valve V1.

During the phase of injection by the gas injection device 4, the gas inlet valve V1 is maintained in an open state. The intake valve 4*d* is then controlled by the control unit 7 or by a specific control module that is part of the pressure regulation system, according to the pressure data detected by the pressure sensor 6, to alternate between allowing the entry of gas from the source 4*a* into the container 2 and preventing such entry. The gas in question is, for example, air or nitrogen ($N_2$). The air or nitrogen is injected into the container 2 for example until the inner filling space Vg reaches a positive pressure between 10 and 50 mbar. "Positive pressure" is understood to mean a pressure greater than the ambient pressure which, to generalize, can be assumed to be equal to the atmospheric pressure.

There is also provided a gas release valve V2 on the gas outfeed section 5*b* of the line 5 between the common section 5*c* and an outlet S to the outside. The gas release valve V2 may be controlled by the control module 9 of the control unit 7, according to the pressure data detected by the pressure sensor 6, to alternate between releasing gas from the container 2 or preventing such release. One will note that during a freezing phase, the gas release valve V2 allows the release of gas to the outlet S.

Referring to FIG. 1, a gas removal valve V3 is arranged on a bypass 5*b* of the gas outfeed section 5*d*, parallel to the gas release valve V2. This gas removal valve V3, which is selectively opened by a control module 9 of the control unit 7, is in a closed state during the injection phase and during a subsequent pressure balancing phase with unrestricted gas release. The equipment 50 for controlling the flow of gas may have valve controllers 50*a*, 50*b*, 50*c* respectively connected to the valves V1, V2, V3 by wired or wireless control lines. Of course, it is also possible to incorporate controller 4*c* into the equipment 50. The control module 9 may coordinate or incorporate the valve controllers 50*a*, 50*b*, 50*c*. It allows controlling the filling of the container 2 with gas, by modifying the state of the valves V1, V2, V3.

The pressure sensor 6 is adapted to detect the gas pressure in the space formed by the upper head portion of the container 2 in the non-limiting example shown in FIG. 1. For example, the pressure sensor 6 will be located in the gas entry/exit line 5, allowing it to detect the gas pressure in the common section 5*c*. The pressure sensor 6 transmits pressure data, measured regularly over time, to the memory 8 of the control unit 7. For example, a wired or wireless transmission line 6*a* can be provided that extends from the pressure sensor 6 to the control unit 7. The pressure sensor 6 detects the pressure in the headspace, or more generally in the inner filling space Vg occupied by the gas.

The control unit 7 here comprises an analysis module 10 for estimating a gas filling control parameter. This parameter is used to determine the amount of gas to be removed. To estimate the inner filling space Vg, it may be necessary to characterize the release of gas throughout the gas passage opening 20. A timer 11 (for example a timer of a known type) is further provided, to supply data to the control unit 7 that are representative of a characteristic duration of the gas release through the passage opening 20 and through the gas release valve V2. The pressure sensor 6 and the possible regulation using this pressure sensor 6 ensure that the pressure level after freezing the biopharmaceutical fluid B is limited to a level lower than a predetermined threshold, for example 100 mbar, preferably less than or equal to 50 mbar. If there is regulation, the pressure level is typically about 35 mbar (0.51 psi).

The timer 11 is activated after the filling by the gas injection device 4 and after the possible freezing is performed, during a decrease in pressure inside the container 2.

In a particular example of preparation of the container 2, the following sequence of steps may be provided for monitoring the gas fill level: filling the container with biopharmaceutical fluid B via the entry port 21, injecting gas into the container 2 with the gas injection device 4 (possibly with regulation), optional freezing of the biopharmaceutical fluid B, controlling a flow of released gas by opening the gas release valve V2, estimating a control parameter representative of the inner filling space Vg during this gas release, and generating a negative pressure by extracting gas (forced flow) from the container 2, knowing that the duration of the extraction is adjusted according to the control parameter.

Referring to FIG. 1, one can see that a pumping device 40 is mounted on the bypass 5*d* to generate a negative pressure in the inner filling space Vg, by forcing gas to flow out of the container 2 when the gas removal valve V3 is in an open state and the gas release valve V2 is in a closed state, such that gas is routed to the outlet S. The following table 1 illustrates an example of controlling the valves V1, V2, V3, and 4*d* in a context of preparing the container 2.

TABLE 1

Valve state during container preparation

|  | V1 | V2 | V3 | 4d |
|---|---|---|---|---|
| Gas injection | Open | Closed | Closed | Open* |
| Gas release (free) | Closed | Open | Closed | Closed |
| Generation of negative pressure | Closed | Closed | Open | closed |

*The intake valve 4d can, where appropriate, be closed temporarily during the injection phase when there is pressure regulation for the container 2.

When the gas removal valve V3 is in the open state, the pumping means 40 extracts the gas at a flow rate F that may be constant, for example about 8 liters per minute. To achieve this, the pumping means 40 typically comprises a vacuum pump 60 or similar device creating a negative pressure in the common section 5c. This pumping means 40 may be coordinated with the control module 9 to adjust the duration of the forced flow according to the control parameter determined by the analysis module 10. Control of the vacuum pump 60 can be provided in a user interface, for example setting the flow rate of the vacuum pump 60 according to the maximum capacity of the container 2 (a flow rate less than or equal to 1 liter per minute being considered sufficient for example for maximum capacities less than or equal to about 2 liters).

It is thus understood that in the non-limiting example of FIG. 1, the plurality of valves (only three valves V1-V3 can be used) is either in a first configuration permitting the flow of gas in the incoming direction, or in a second configuration permitting the flow of gas in the outgoing direction. Although this example shows the use of the same gas passage opening 20 for the gas flow, one can of course consider one-way flows using two separate openings. It is considered advantageous, however, to use a single opening for the gas flow for reasons that include simplicity in the design of the container 2 and in connection to the rest of the facility.

A detailed and non-limiting example is described below, concerning adjusting the removal of gas until a desired level of negative pressure is reached, for the case of removing 40% of gaseous material from the inner filling space Vg. The term negative pressure is also used as being relative to ambient pressure.

In a container 2 as shown in FIG. 1 and having a maximum capacity of 119 L, the measured level of positive pressure of the inert gas or air is, for example, 35 mbar. The filling level N is not precisely known and typically can vary between a relatively extreme case of a low filling level of only 25 L of biopharmaceutical fluid B in the liquid state (which is 27 L in the solid state), and a filling level above 100 L (given that a volume of 101 L of biopharmaceutical fluid in the liquid state is typically 110 L in the solid state). In other words, the inner filling space Vg occupied by the gas in the headspace can vary between 9 L and 92 L.

To determine the inner filling space Vg, the control unit 7 is configured in advance, for example via a user interface, with a first level of positive pressure OP1 and a second level of positive pressure OP2. In this example, the input parameters are selected as follows:

OP1=20 mbar (preset level within the 1-50 mbar range);
OP2=5 mbar (preset level within the 1-50 mbar range).

Other parameters related to the dimensions of the gas entry/exit line 5 and to invariable dimensions characteristic of the container 2 may be taken into account. Accommodation of these additional parameters will not be detailed here.

The pressure regulation system is disabled. The gas release valve V2 is open.

The duration $\Delta t$ of the gas release necessary between detection of the first level of positive pressure OP1 and detection of the second level of positive pressure OP2 by the pressure sensor 6 is determined by the timer 11. It is understood that the pressure sensor 6 can obtain several measurements close together of a gas parameter representative of the pressure level in the inner filling space Vg, the output signals or one continuous output signal typically being delivered by the pressure sensor 6 to the control unit 7. For example, starting the operation of the timer 11 is dependent on a signal indicating detection of the first level of positive pressure OP1, received by the control unit 7, while stopping the operation of the timer 11 depends on a signal indicating detection of the second level of positive pressure OP2, received by the control unit 7.

In the present example, the duration $\Delta t$ of the gas release is 50 seconds. In one embodiment of the control unit 7, an algorithm is provided for calculating the inner filling space Vg or an equivalent control parameter, from the input parameters given above and from this duration $\Delta t$ of the gas release. A routine for implementing this algorithm is for example stored in memory 8 and activated by the analysis module 10. The control parameter, via the analysis module 10, allows determining a setting that can be taken into account by the control module 9 for pumping the gas. The algorithm may carry out two successive calculation steps:

calculating a decay constant k, characteristic of the flow of released gas, according to the following equation:

$$k=-\ln(OP2/OP1)/\Delta t$$

where ln is the natural logarithm function.

calculating the inner filling space V2 by using the following correlation:

$$Vg=Q/k+Vc$$

where Q is a volumetric flow rate constant and Vc is a volume constant, these two constants Q and Vc being experimentally determined from experiments in which the internal volume Vg is already known for a similar container 2, during a prior calibration process. With the parameters Vg and the inverse 1/k being considered as inputs to the above linear regression, we experimentally obtain the constants Q and Vc as output values. The correlation corresponds to the physical gas flow model applicable to the release of gas through the passage opening 20 and via the gas release valve V2.

The two constants Q and Vc may specifically depend on the dimensions of the facility 1 and/or on the biopharmaceutical fluid B filling parameters of the container 2 which can be considered as unchanging. For this correlation relating to the volume, obtained by simple linear regression, the constant Q is a slope or gradient (called the "volume estimator slope"), while the constant Vc is the intercept (called the "volume estimator intercept").

In experimental conditions where the constant Q was evaluated at 0.288 L/s (17.28 L/min) and the constant Vc was evaluated at 5.066 L, and for the above case where the duration $\Delta t$ of the gas release determined by the control unit 7 is 50 seconds to transition from 20 mbar to 5 mbar, calculation with the algorithm yields a value for k as follows:

$$k=-\ln(5/20)/50=0.00277 \text{ s}^{-1}$$

Next, the inner filling space Vg is estimated as 15.5 L using the following calculation, taking into account the values for constants Q and Vc as indicated above:

$$Vg=0.288/0.0277+5.066$$

When the control unit 7 has such a control parameter, it is then permissible to use the control parameter when controlling a forced flow of gas between the gas passage opening 20 and the outlet S. This forced flow is achieved by pumping, for example at a constant flow rate F at the pumping device 40, for a desired period of time which takes the control parameter into account. In an exemplary embodiment, the forced flow is stopped after a first time limit corresponding to the time required to release an amount of gas equal to 30% of the initial amount contained in the inner filling space Vg determined by the control unit 7, and before a second time limit corresponding to the time required to release an amount of gas equal to 50% of this initial amount as determined by the control unit 7. By taking a target corresponding to 40% of the amount of gas, the desired duration can be simply calculated based on the flow rate F when pumping. For a flow rate F of 8 L/min, we obtain:

$$\text{Desired duration}=Vg/F\times 40/100=15.5/8\times 0.4=0.78 \text{ min}=47 \text{ s}$$

This type of calculation, which can correspond to a supplemental calculation step of the algorithm, is performed assuming a constant temperature, as the temperature variation is negligible under the normal operating conditions of the container 2 preparation method. After pumping, the container 2 can be detached from the rest of the facility, the ports 20-22 being hermetically sealed in a known manner (the ports may include check valves or backflow preventer valves or other similar sealing systems).

The desired duration is directly proportional to the target percentage, which is 40% here. Removing approximately 40% of the gas is considered a good compromise that accommodates extreme pressure variation conditions, particularly those resulting from a change of altitude. An environmental variation in pressure caused by an altitude gain of the sealed container 2 of about 3000-4000 meters can thus advantageously be absorbed by the initial negative pressure in the container 2 prepared as described above.

The act of freely releasing the gas (which tends toward a pressure level in equilibrium with the surrounding pressure) and then selectively removing a desired fraction of the remaining gas, is not only advantageous in the case of container preparation with prior freezing. Indeed, for certain reactive liquids under conditions requiring gas pressurization (for example reactive when exposed to air), it is also desirable to remove a fraction of the gas from the inner filling space Vg before shipping.

Alternatively, the gas filling control parameter can be determined during a process of freezing the container contents. In this embodiment, during the freezing process, the pressure sensor 6 regularly measures the pressure inside the container 2 over time. Note that in the present case, we consider the container to be closed during the entire freezing process.

When the amount of gaseous material is constant, a law can be applied that relates the gas volume and the measured pressure. The ideal gas law can be used for example, although more complex laws are possible. As an illustration, for the ideal gas law, the volume V is written as a function of the pressure P as follows: $V=k_g/P$, where $k_g$ is considered to be constant over time. In particular, $k_g=nRT$, where T is the temperature, considered to be substantially constant during freezing, n is the number of moles of gas, and R is the gas constant.

Therefore, the change in volume over time is written as $dV/dt=k_g \cdot d(1/P)/dt$, where 1/P denotes the inverse pressure function, d(1/P)/dt denotes the derivative of this function over time, and dV/dt the derivative of the volume over time.

Thus, from measuring the value of P over time, the analysis module 10 can determine the function 1/P over time, and its derivative function. The derivative function may be filtered by a suitable filter to eliminate certain measurement noise. Integration of the filtered derivative function over time allows determining the change in the gas volume during the freezing process. This change in the gas volume can be used as a control parameter for determining the pumping characteristics. For example, by integrating this curve over time, the volume of gas after the freezing process can be determined.

A facility with another type of container 2, specially adapted for thermal treatment, will now be described with reference to FIG. 2.

Here, the storage unit for biopharmaceutical use has a flexible container 2, received and externally supported in a rigid receiving and support structure 30. The flexible container 2 comprises a flexible envelope 25 which defines an interior space capable of receiving content and here having actually received it.

Such a container 2, such as might be used with the system of FIG. 3, is typically a 3D bag with the volume of the interior space possibly being at least 50 liters, up to 3,000 liters or more. Such a 3D bag is described in WO00/04131A1 or is commercially available under the brand Flexel® 3D. Containers of smaller volume also exist, such as those shown in FIG. 4.

The flexible container 2 is usually provided with ports similarly to the first embodiment, for example such as the entry port 21 for introducing a product to be mixed with the content of the container 2, located in the upper portion 2a, the exit port 22 for discharging the mixed product from the container 2, a gas passage opening or port 20, and where appropriate a port 20' for mounting a functional device or measurement means, for example for measuring a parameter indicative of or related to the homogeneity, the heterogeneity, or the blending of the content in the interior space.

It will be understood that the preparation of the interior of the container 2 can be carried out in a similar manner by means similar to those described with reference to FIG. 1. The control unit 7 shown in FIG. 2 may thus be similar or functionally identical to the one shown in FIG. 1, for adjusting the removal of gas until a desired pressure level is reached. The description of the gas injection device 4, the valves V1-V3, and the pumping means 40 will therefore not be repeated and it is understood that the estimation of the control parameter can be identical or similar to what has been described above. Therefore for this second embodiment, only the design details specifically concerning the storage unit for biopharmaceutical fluid B will be described below.

Figure 2:
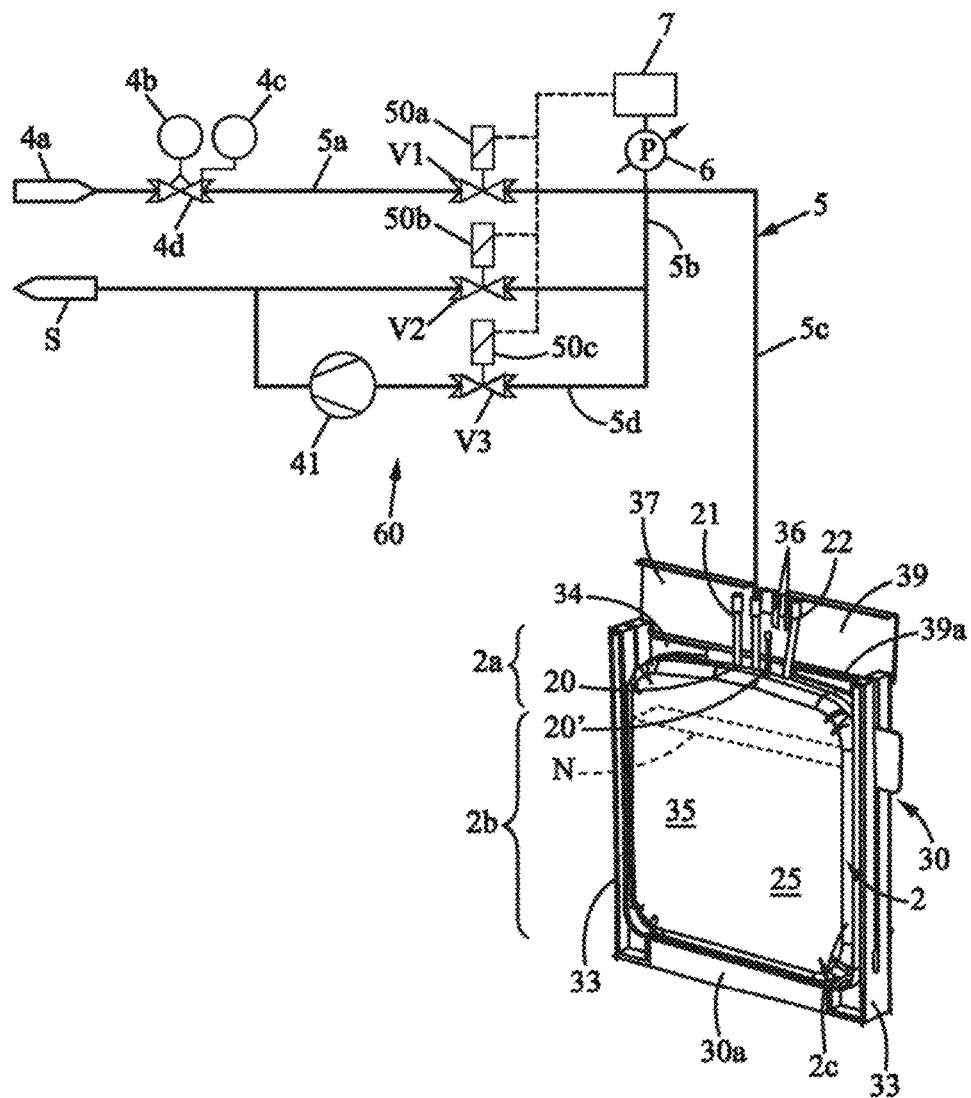
FIG. 2 is a perspective view schematically illustrating a portion of a facility for preparing a container according to a second embodiment.

Referring to FIG. 2, the rigid receiving and support structure 30 typically comprises, as shown here, a lower bottom wall 30a, arranged horizontally, and a side wall 33, arranged vertically, and an opening 34 in the upper portion for the insertion and removal of the flexible container 2. The rigid receiving and support structure 30 defines an interior space 35 accessible through the opening 34. This space 35 receives and externally supports the flexible container 2 such that the lower portion 2b and side portion 2c of its flexible envelope 25 press against the inside face of the bottom wall 30a and side wall 33. In addition, the rigid receiving and support structure 30 is usually provided with holes 36 which can cooperate with the ports of the flexible container 2. Where appropriate, the rigid receiving and support structure 24 also comprises restraining means 37 suitable for being applied against the upper portion 2a of the flexible container 2.

The restraining means 37 may, for example, comprise a restraining flap 39 pivoting on the side walls 33 by means of a hinge 39a, between an open position shown in FIG. 2 and a closed position where the flap 39 extends substantially horizontally and is locked to retain the container 2 within the interior space 35. The flap 39 comprises slots including the holes 36 providing access to the ports 20-22 and 20'.

The principles of the layout and implementation of such a rigid storage unit (which receives and supports the flexible container 2) are part of the general knowledge of or are within the reach of the skilled person. In all cases, the rigid receiving and support structure 30 is rigid and constitutes a fixed, non-deformable part supporting the flexible container 2. Of course, the storage unit can be transported and possibly disassembled or folded.

Alternatively and as illustrated in FIG. 3, such a rigid structure 30 can be replaced with a rigid receptacle 55 that is open at its upper end and defines a cavity 55a. This can be the case for containers of smaller dimensions in particular, holding several liters or so (1-5 liters) and easier to handle. In such a case, the container 2 can be placed in the rigid receptacle 5 for the handling operations.

FIG. 3 shows such a receptacle 55, specially adapted for receiving a container 2 loaded with a biopharmaceutical fluid B as described above. The receptacle 55 comprises a body 56 defining the cavity 55a. The body 56 comprises an inner wall 41 extending from an open upper end to a lower base. The inner wall 41 defines a contact surface for the container 2. The body 56 also comprises an outer wall 42 extending downward from an upper end at the upper end of the inner wall 41. The inner wall 41 and outer wall 42 define between them a plurality of pockets 43, which are cavities extending between the inner wall 41 and outer wall 42 from top to bottom. It may be arranged, for example, that the inner wall 41 is substantially flat on each longitudinal side of the cavity 55a, and that on this same side, the outer wall 42 has a regular slotted profile, two slots together with the inner wall 41 defining a pocket 43.

Referring to FIG. 3, the thermal treatment unit for performing the freezing operation may comprise a stand 44 on which the receptacle 55 is placed. Mechanical retention of the receptacle 55 on the stand 44 may be provided for example. For example, the receptacle 55 and the stand 44 have complementary shapes that cooperate. In the example shown, the stand 44 comprises a groove 45 in its upper face 46. The receptacle 55 comprises a projecting portion 47 inserted into the groove 45. For example, the projecting portion 47 is provided on each narrow side face of the outer wall 42. Thus, the projecting portions 47 are inserted into the grooves 45 formed in the upper face 46 of the stand 47, and the bottom of the pockets 43 rests on this upper face 46.

We have described here a stand 44 accommodating a receptacle 55. As can be seen in FIG. 3, the stand 44 can accommodate several receptacles 55, placed for example adjacent to each other on the stand 44. In other words, the thermal treatment unit can apply a thermal treatment to a plurality of containers 2 simultaneously.

The thermal treatment process can thus be carried out for example as described in WO 2011/063381, by using applicator elements that enter the pockets 43, the container 2 having been previously placed in the receptacle 55. After a certain amount of time, once the thermal treatment is complete, the applicators elements can be withdrawn in a manner that reverses their insertion.

The invention has been described above for a particular embodiment of containers 2 and preparation device 3. However, the invention is not limited to these embodiments. Alternatively, other types of containers and/or other types of preparation means may be used.

For example, in one particular embodiment, the container 2 may be rigid or non-deformable, at least in a portion enclosing the main portion of the biopharmaceutical fluid B. At least one pressure level in the container 2 headspace can be used as the macroscopic control parameter, without having to specifically determine the inner filling space Vg occupied by the gas. In another particular embodiment, the envelope 25 of the container 2 can be extensible. A parameter combining the pressure in the headspace of the container 2 and the volume of the envelope 25 can be used as the control parameter.

FIG. 4 shows yet another exemplary embodiment of the storage unit for biopharmaceutical fluid B. As in the previous embodiments, the container 2 comprises an envelope and a structure 30. Here the structure 30 is made in two independent parts 73 and 74 that can be assembled together, the container 2 being arranged between the two parts 73 and 74. In this example, each part 73 is in the form of a shell forming a frame defining a central opening 75, 76 respectively, through which the container 2 protrudes. The head portion of the container 2 is equipped with two lines for filling 54a and draining 54b which are arranged between the two parts 73 and 74 forming a shell and are protected by them. The gas entry/exit lines 5 are not represented in this example, but may be provided in parallel. The bottom part of the flexible container 2 may be equipped with a port 77 where a local temperature sensor or any other desired instrumentation can be mounted.

Figure 6:
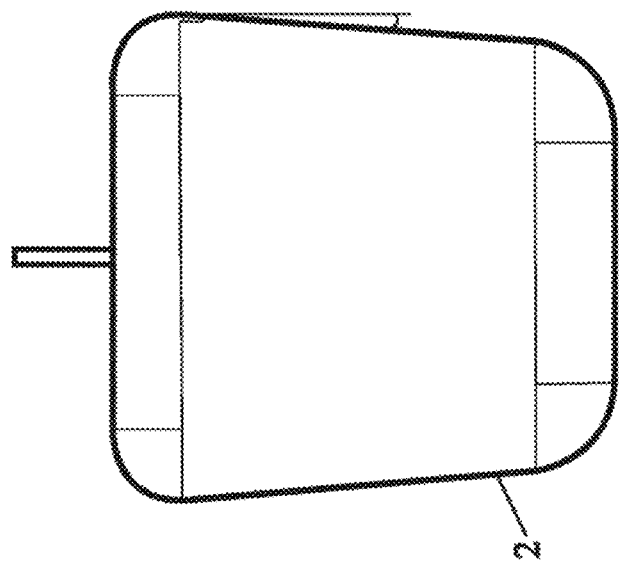
FIG. 6 is a front view of FIG. 5.
Figure 5:
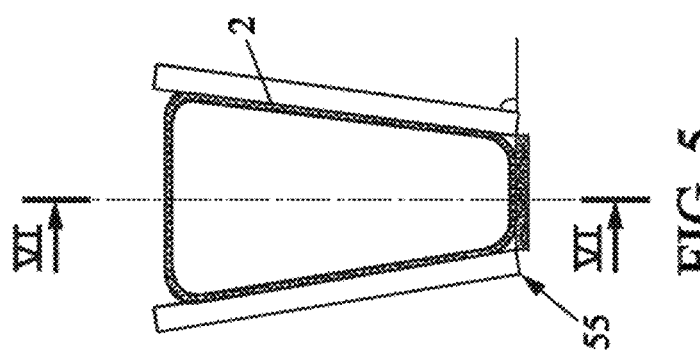
FIG. 5 is a schematic side view of a portion of a storage unit according to another embodiment usable in the facility.

FIGS. 5 and 6 show yet another alternative embodiment, respectively in a side view and front view. In this embodiment, one difference from the preceding examples is that the receptacle 55 of the thermal treatment facility has, in a cross-sectional view, a shape that flares slightly outward in the upward direction along the vertical axis. The storage unit may have a shape appropriate for this form of receptacle. In particular, the container 2 may have a greater width in its upper portion than in its lower portion. In addition, as can be seen in FIG. 6, the receptacle 55 of the thermal treatment facility may also have, in an orthogonal cross-sectional view, a shape flaring slightly outward in the upward direction along the vertical axis. The storage unit may have a shape appropriate for this form of receptacle. In particular, the container 2 may also have a greater width in its upper portion than in its lower portion in this view. The structure 30 of the storage unit is appropriate for the shape of the container 2. The advantage of this flared shape is that it provides better control of how the freezing front spreads during the fluid's transition from the liquid state to the solid state during cold treatment.

One advantage of preparing the container with an adjustment of the negative pressure within the inner filling space Vg occupied by the gas is that it is not necessary to know the mass, density, or volume of the biopharmaceutical fluid. The preparation method thus allows packaging with sufficient pressure to anticipate reliably (without manual intervention on the container 2 by an operator) the possible pressure variations, including the possibility of anticipating the most extreme variations during shipping conditions.

The invention claimed is:

1. Facility for the preparation of a container loaded with a biopharmaceutical fluid, wherein the facility comprises:
   a fluidtight container in which is placed a biopharmaceutical fluid and a gas which occupies an inner filling space, the container comprising a gas passage opening and being adapted to be filled with gas to an initial level of positive pressure in the inner filling space;
   a control module for controlling the filling of the container with gas;
   an analysis module for estimating a gas filling control parameter; and
   a pumping means for generating a negative pressure in the inner filling space by forcing the gas to flow out of the container via the gas passage opening, the control module and the pumping means being coordinated to adjust the duration of the forced flow on the basis of the control parameter determined by the analysis module.

2. Facility according to claim 1, wherein the control module is adapted to selectively control a flow of released gas through the gas passage opening of the container, so as to reduce the pressure level in the inner filling space, and the gas filling control parameter is representative of said inner filling space, the analysis module being configured to estimate said control parameter by monitoring the flow of released gas between a first level of positive pressure OP1 and a second level of positive pressure OP2 in the inner filling space.

3. Facility according to claim 2, wherein the analysis module comprises or is connected to a timer adapted to determine the duration of the gas release Δt required to drop from the first level of positive pressure OP1 to the second level of positive pressure OP2.

4. Facility according to claim 2, wherein the analysis module determines, as the control parameter, the inner filling space using the following correlation:

$$Vg=Q/k+Vc$$

where:
   Vg is the inner filling space occupied by the gas;
   Q is a volumetric flow rate constant;
   Vc is a volume constant;
   k is a decay constant;
   knowing that the decay constant is calculated using the equation:

$$k=-\ln(OP2/OP1)/\Delta t$$

with
   OP1 being the first level of positive pressure inside the container;
   OP2 the second level of positive pressure inside the container;
   Δt being the duration of the gas release required to drop from the first level of positive pressure OP1 to the second level of positive pressure OP2;
   ln representing the natural logarithm function.

5. Facility according to claim 1, further comprising a plurality of valves comprising valves selectively controlled by the control module and having:
   a first configuration permitting the flow of gas in an incoming direction into the container; and
   a second configuration permitting the flow of gas in an outgoing direction from the container;
   the control module being adapted to successively configure the first configuration to enable the container to be filled with gas to a state of positive pressure within said inner filling space, and the second configuration to enable gas to escape from the container via its gas passage opening at most until a state of pressure equilibrium is reached in said inner filling space.

6. Facility according to claim 5, wherein said plurality of valves comprises a first gas inlet valve selectively opened by the control module in the first configuration and a second gas release valve selectively opened by the control module in the second configuration, the gas inlet valve and the gas release valve being in fluid communication with said gas passage opening.

7. Facility according to claim 5, wherein the pumping means comprises a vacuum pump and a third gas removal valve that is one among said plurality of valves, the control module being configured for selectively opening the gas removal valve and closing the gas inlet valve and the gas release valve when the vacuum pump is actuated.

8. Facility according to claim 1, wherein the analysis module comprises or is connected to a pressure sensor in fluid communication with the gas passage opening and adapted for measuring a level of positive pressure inside the container.

9. Facility according to claim 1, comprising a gas injection device adapted to inject gas, into the container by said gas passage opening prior to the control parameter determination.

10. Facility according to claim 9, wherein the gas injection device, the pumping means, and a control unit comprising the control module and the analysis module are incorporated into a device for preparing the interior of the container.

11. Facility according to claim 9, wherein the gas is pressurized gas.

12. Facility according to claim 1, wherein the container is flexible and sealed closed, the container comprising gas-impermeable plastic walls.

13. Method for preparing a sealed container loaded with a biopharmaceutical fluid, a gas occupying an inner filling space inside the container at an initial level of positive pressure, wherein the gas filling level within the container is controlled, the method comprising the steps of:
   b) estimating a gas filling control parameter which is representative of said inner filling space,
   c) generating a negative pressure in the inner filling space by forcing gas to flow out of the container, the duration of the forced flow being adjusted according to said control parameter.

14. Method according to claim 13, wherein the forced flow is achieved by pumping at a constant flow rate, the forced flow being stopped after a first time limit corresponding to the time required to discharge an amount of gas equal to 30% of the initial amount of gas contained in the inner filling space determined in step b) and before a second time limit corresponding to the time required to evacuate an amount of gas equal to 50% of the initial amount of gas contained in the inner filling space determined in step b).

15. Method according to claim 13, further comprising the following step before step b):
   a) selectively controlling a flow of released gas through a gas passage opening of the container, so as to lower the positive pressure inside the container; and wherein the estimating in b) includes monitoring the flow of released gas between a first level of positive pressure OP1 and a second level of positive pressure OP2 in the inner filling space.

16. Method according to claim 15, wherein said control parameter is estimated by determining the duration of the gas release Δt required to drop from the first level of positive pressure OP1 to the second level of positive pressure OP2.

17. Method according to claim 13, comprising, prior to step a), the steps of:
   injecting a gas into the container until a positive pressure is reached in the inner filling space of between 10 and 50 mbar; and
   freezing the biopharmaceutical fluid.

18. Method according to claim 17, wherein the gas is air or nitrogen.

19. Method according to claim 13, wherein step b) is performed when a gas release valve in fluid communication with the gas passage opening is selectively opened, said gas release valve remaining open until the pressure between the inner filling space and the environment is equalized, several measurements of a parameter of the gas representative of a level of positive pressure in the inner filling space being performed during step b).

* * * * *